United States Patent [19]

Munayyer et al.

[11] Patent Number: 4,808,610

[45] Date of Patent: Feb. 28, 1989

[54] MOMETASONE FUROATE ANTI-INFLAMMATORY CREAM COMPOSITION USING HEXYLENE GLYCOL

[75] Inventors: Farah J. Munayyer, West Caldwell, N.J.; Joel A. Sequeira, New York, N.Y.

[73] Assignee: Schering Corporation, Kenilworth, N.J.

[21] Appl. No.: 914,227

[22] Filed: Oct. 2, 1986

[51] Int. Cl.[4] .............................................. C07D 31/58
[52] U.S. Cl. .................................... 514/172; 514/887
[58] Field of Search ........................................ 514/172

[56] References Cited

U.S. PATENT DOCUMENTS

| | | | |
|---|---|---|---|
| 4,070,462 | 1/1978 | Ecker | 514/179 |
| 4,124,707 | 11/1978 | Green et al. | 514/180 |
| 4,201,778 | 5/1980 | Draper | 514/180 |
| 4,267,173 | 5/1981 | Draper | 514/180 |
| 4,472,393 | 9/1984 | Shapiro | 514/176 |

*Primary Examiner*—Mark L. Berch
*Attorney, Agent, or Firm*—John J. Maitner; Stephen I. Miller; Gerald S. Rosen

[57] ABSTRACT

Disclosed is an elegant, stable, self-preserving cream formulation containing mometasone furoate, 9α, 21-dichloro-16α-methyl-1,4-pregnadiene-11β,17α-diol-3,20-dione-17-(2'-furoate), useful as a topical anti-inflammatory product.

6 Claims, No Drawings

MOMETASONE FUROATE ANTI-INFLAMMATORY CREAM COMPOSITION USING HEXYLENE GLYCOL

This invention relates to a cream formulation of mometasone furoate, $9\alpha,21$-dichloro-$16\alpha$-methyl-1,4-pregnadiene-$11\beta,17\alpha$-diol-3,20-dione-17-(2'-furoate).

U.S. Pat. No. 4,472,393 discloses 3,20-dioxo-1,4-pregnadiene-$17\alpha$-ol-17-aromatic heterocycle carboxylate compounds, pharmaceutical compositions containing said compounds and methods for the treatment and control of inflammatory conditions with said compounds. Included in the compounds disclosed in this patent is mometasone furoate which is insoluble in water and has poor solubility in solvents frequently utilized in topical preparations. Such poor solubility characteristics hindered the development of a cosmetically elegant cream with superior anti-inflammatory activity.

When the drug was partially dissolved and partially suspended in propylene glycol based cream formulations, the resulting formulations did not possess the necessary efficacy. When the drug was completely dissolved in oleyl alcohol/propylene glycol based cream formulations, the resulting formulations not only lacked the required activity but also were found to be irritating in a rabbit dermal test. Additionally, various cream formulations containing a variety of drug solubilizing agents resulted in poor activity.

The formulation of the present invention provides a cream formulation having cosmetic elegance and outstanding efficacy. The formulation is of value in the topical treatment of dermatological disorders such as contact and allergic dermatitis, eczemas and psoriasis. Treatment with the formulation of this invention is usually accomplished by applying it to completely cover the affected area. The usual frequency of application is once daily, although adequate maintenance therapy for some patients may be achieved with less frequent application.

The formulation of the present invention is a unique drug co-solvent-in-oil emulsion for administration to warm-blooded animals, including man, containing as the active anti-inflammatory ingredient an effective amount of mometasone furoate. The internal phase of the emulsion is the drug co-solvent component comprising the hexylene glycol water mixture. In addition to the active ingredient, pharmaceutically acceptable adjuvants, stabilizers, preservatives, whiteners, buffers and surfactants are used in the formulation of this invention.

The formulation of the present invention comprises:
0.01 to 0.25 percent Mometasone Furoate
5 to 20 percent Hexylene Glycol NF
1.0 to 5.0 percent Water Purified USP
2.0 to 10.0 percent White Wax NF
4 to 12 percent of a lipophilic emulsifier having a HLB below 5.
0.7 to 4 percent of a hydrophilic emulsifier having a HLB above 11
0.2 to 2.0 percent Titanium Dioxide USP
5 to 20 percent Aluminum Starch Octenylsuccinate
40 to 70 percent White Petrolatum USP Sufficient acid is added to adjust the pH of the purified water to pH $2.5 \pm 0.2$; charged as a 10% w/v solution. Examples of acids which can be utilized in the cream formulation are phosphoric acid, hydrochloric acid, acetic acid, and the like. The preferred acid is phosphoric acid.

In a preferred aspect of the present invention, the formulation comprises:
0.05 to 0.15 percent Momentasone Furoate
9 to 15 percent Hexylene Glycol NF
2 to 4 percent Water Purified USP
4 to 6 percent White Wax NF
6 to 10 of a lipophilic emulsifier having a HLB below 5
1.2 to 2.5 percent of a hydrophilic emulsifier having a HLB above 11
0.75 to 1.25 percent Titanium Dioxide USP
8 to 12 percent Aluminum Starch Octenylsuccinate
50 to 60 White Petrolatum USP This formulation results in an elegant stable, water-washable cream with excellent anti-inflammatory activity. This cream is also self-preserving.

The preferred lipophilic emulsifier is propylene glycol stearate. Other acceptable lipophilic emulsifiers for use in the cream include ethylene glycol monolaurate, ethylene glycol monostearates, propylene glycol monolaurate and glyceryl monoricinolate.

The preferred hydrophilic emulsifier is Ceteareth-20, i.e. polyethylene glycol ether of cetearyl alcohol that conforms generally to the formula $R(OCH_2CH_2)_nOH$ wherein R represents a blend of cetyl and stearyl radicals and n has an average value of 30. Other acceptable hydrophilic emulsifiers for use in the cream include polyethylene glycol monolaurate, polyethylene glycol distearate, P.O.E. cetyl alcohol, P.O.E. sorbitan monostearate and P.O.E. sorbitan monooleate.

The HLB is defined by Griffin, W. C., J. Soc. Cosmetic Chemist, 1,311 [1949] and 5,249 [1949]. The HLB reflects the balance between hydrophilic and lipophilic strength of the emulsifiers. The higher HLB, indicates a stronger hydrophilic tendency of the emulsification system.

The formulations of the present invention are manufactured in a conventional manner by thoroughly mixing the ingredients at ambient or elevated temperatures. Preferably, the mometasone furoate, dissolved in a portion of the hexylene glycol/water mixture is added to the oil phase. The ingredients are thoroughly mixed so that the product is homogeneous. Processing equipment suitable for preparing the cream are known in the art and include colloid mills, homogenizers, roller mills, propeller mixers and the like.

All percentages are by weight. The definitions of components whose chemical composition is not immediately clear from the name used, such as "Ceteareth-20" and "Promulgen-G"., may be found in the CTFA Cosmetic Ingredients Dictionary, 3rd Edition, published by Cosmetic Toiletry and Fragrance Association, Inc., Washington, DC.

The following formulation examples illustrate the compositions of the present invention. It will be apparent to those skilled in the art that many modifications thereof may be practical without departing from the purpose and intent of this disclosure.

EXAMPLE 1

An anti-inflammatory cream is prepared from the following ingredients:

| Ingredients | Quantity, mg/g |
|---|---|
| Mometasone Furoate | 1.0 |
| Hexylene Glycol NF | 120 |

-continued

| Ingredients | Quantity, mg/g |
| --- | --- |
| Water Purified USP | 30 |
| White Wax NF | 50 |
| Propylene Glycol Stearate | 80 |
| Stearyl Alcohol and Ceteareth-20 (Promulgen-G) | 70 |
| Titanium Dioxide USP | 10 |
| Aluminum Starch Octenylsuccinate | 100 |
| Phosphoric Acid NF | ** |
| White Petrolatum USP | 539 |

**Used to adjust the pH of the purified water to pH 2.5 ± 0.2; charged as a 10% w/v solution.

Procedure

1. In a suitable vessel charge the white petrolatum, white wax, propylene glycol stearate and Promulgen-G. Melt and heat to 70° C. with agitation until a homogenous melted mixture is obtained.

2. In a separate vessel, prepare a 10% w/v phosphoric acid solution.

3. Charge the purified water to a suitable vessel and adjust the pH of the water to about 2.5 with 10% phosphoric acid solution.

4. Charge the hexylene glycol to the acidified water and adjust the pH to 4.0 by addition of the 10% phosphoric acid solution, only if necessary.

5. Dissolve the mometasone furoate in approximately 90% of the hexylene glycol/water at 60°-65° C. Heat the solution to 70° C. and charge to the mixture prepared in Step 1. Mix to achieve adequate emulsification at 70° C.

6. Rinse containers used for the active solution with the remaining 10% hexylene glycol/water and add rinse to the emulsion prepared in Step 5.

7. Charge the titanium dioxide and aluminum starch octenylsuccinate in small portions to Step 5 at 70° C. and mix for at least twenty minutes.

8. Cool the batch to approximately 25° C. with appropriate mixing and add to appropriate containers.

EXAMPLE 2

An anti-inflammatory cream is prepared from the following ingredients:

| Ingredients | Quantity, mg/g |
| --- | --- |
| Mometasone Furoate | 0.5 |
| Hexylene Glycol NF | 60.0 |
| Water Purified USP | 15.0 |
| White Wax NF | 60.0 |
| Propylene Glycol Stearate | 70.0 |
| Stearyl Alcohol and Ceteareth-20 (Promulgen-G) | 60.0 |
| Titanium Dioxide USP | 10 |
| Aluminum Starch Octenylsuccinate | 100 |
| Phosphoric Acid NF | ** |
| White Petrolatum USP | 624.5 |

**Used to adjust the pH of the purified water to pH 2.5 ± 0.2; charged as a 10% w/v solution.

The procedure for preparing the cream is as described in Example 1.

EXAMPLE 3

An anti-inflammatory cream is prepared from the following ingredients:

| Ingredients | Quantity, mg/g |
| --- | --- |
| Mometasone Furoate | 1.0 |
| Hexylene Glycol NF | 120.0 |
| Water Purified USP | 30.0 |
| Microcrystalline Wax | 50.0 |
| Propylene Glycol Stearate | 80.0 |
| Stearyl Alcohol and Ceteareth-20 (Promulgen-G) | 70.0 |
| Titanium Dioxide USP | 8.0 |
| Aluminum Starch Octenylsuccinate | 120.0 |
| Hydrochloric Acid NF | ** |
| White Petrolatum USP | 521.0 |

**Used to adjust the pH of the purified water to pH 2.5 ± 0.2; charged as a 10% w/v solution.

The procedure for preparing the cream is as described in Example 1.

EXAMPLE 4

An anti-inflammatory cream is prepared from the following ingredients:

| Ingredients | Quantity, mg/g |
| --- | --- |
| Mometasone Furoate | 1.0 |
| Hexylene Glycol NF | 120.0 |
| Water Purified USP | 30.0 |
| White Wax NF | 50.0 |
| Sorbitan Trioleate | 80.0 |
| Stearyl Alcohol and Ceteareth-20 (Promulgen-G) | 70.0 |
| Titanium Dioxide USP | 5.0 |
| Aluminum Starch Octenylsuccinate | 150.0 |
| Phosphoric Acid NF | ** |
| White Petrolatum USP | 494.0 |

**Used to adjust the pH of the purified water to pH 2.5 ± 0.2; charged as a 10% w/v solution.

What is claimed is:

1. A topical pharmaceutical composition for the treatment of inflammation comprising:
   (a) 0.01 to 0.25 percent Mometasone Furoate
   (b) 5 to 20 percent hexylene glycol
   (c) 1.0 to 5 percent water
   (d) 2.0 to 10.0 percent white wax
   (e) 4 to 12 percent of a lipophilic emulsifier having a HLB below 5
   (f) 0.7 to 4 percent of a hydrophilic emulsifier having a HLB above 11
   (g) 0.2 to 2.0 percent Titanium dioxide
   (h) 5 to 20 percent aluminum starch octenylsuccinate
   (i) 40 to 70 percent white petrolatum
   (j) sufficient acid to adjust the pH of the water to pH 2.5 to ±0.2.

2. The topical pharmaceutical composition of claim 1 wherein:
   (a) 0.05 to 0.15 percent Mometasone Furoate
   (b) 9 to 15 percent hexylene glycol
   (c) 2 to 4 percent water Purified
   (d) 4 to 6 percent white wax
   (e) 6 to 10 percent of a lipophilic emulsifier having a HLB below 5
   (f) 1.2 to 2.5 percent of a hydrophilic emulsifier having a HLB above 11
   (g) 0.75 to 1.25 percent titanium dioxide
   (h) 8 to 12 percent aluminum starch octenylsuccinate
   (i) 50 to 60 percent white petrolatum
   (j) sufficient acid to adjust the pH of the water to pH 2.5±0.2.

3. The topical pharmaceutical composition of claim 1 wherein the acid utilized to adjust the pH of the water of phosphoric acid, hydrochloric acid or acetic acid.

4. The topical pharmaceutical composition of claim 3 wherein the lipophilic emulsifier is propylene glycol stearate, ethylene glycol monolaurate, ethylene glycol monostearate, propylene glycol monolaurate or glyceryl monoricinolate.

5. The topical pharmaceutical composition of claim 4 wherein the hydrophilic emulsifier is stearyl alcohol and ceteareth-20, polyethylene glycol monolaurate, polyethylene glycol distearate, P.O.E. cetyl alcohol, P.O.E. sorbitan monostearate or P.O.E. sorbitan monooleate.

6. The topical pharmaceutical composition for the treatment of inflammation comprising:

|     |                                                                         | mg/gram |
| --- | ----------------------------------------------------------------------- | ------- |
| (a) | Mometasone Furoate                                                      | 1.0     |
| (b) | Hexylene Glycol NF                                                      | 120     |
| (c) | Water Purified USP                                                      | 30      |
| (d) | White Wax NF                                                            | 50      |
| (e) | Propylene Glycol Stearate                                               | 80      |
| (f) | Stearyl Alcohol and Ceteareth-20 (Promulgen-G)                          | 70      |
| (g) | Titanium Dioxide USP                                                    | 10      |
| (h) | Aluminum Starch Octenylsuccinate                                        | 100     |
| (i) | White Petrolatum USP                                                    | 539     |
| (j) | Sufficient Phosphoric Acid NF to adjust the pH of the water to pH 2.5 ± 0.2. |         |

* * * * *